US00PP08974P

United States Patent [19]

Van der Jagt

[11] Patent Number: Plant 8,974

[45] Date of Patent: Nov. 8, 1994

[54] CHRYSANTHEMUM PLANT NAMED CORAL REAGAN

[75] Inventor: Martinus Van der Jagt, Langeraar, Netherlands

[73] Assignee: Chrysanthemum Breeders Association, N.V., Netherlands Antilles

[21] Appl. No.: 101,275

[22] Filed: Aug. 29, 1993

Related U.S. Application Data

[63] Continuation of Ser. No. 780,292, Oct. 22, 1991, abandoned.

[51] Int. Cl.[5] ..... A01H 5/00

[52] U.S. Cl. ..... Plt./82.3

[58] Field of Search ..... Plt. 74.1, 82.2, 82.3

[56] References Cited

PUBLICATIONS

Datta, 1991, "Evaluation of recurrent irradiation on vegetatively propagated ornamentals: Chrysanthemum", J. Nuclear Agric. Biol., 20(2): 81–86.

Banerji, et al., 1990, "Induction of somatic mutation in chrysanthemum cultivar 'Anupam'", J. Nuclear Agric. Biol. 19:252–256.

"Mutation Studies on chrysanthemum", NBRI Newsletter, 1989, 16(1):2–3.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in The Improvement of Vegetatively Propagated Crops", Elsevier Sci. Pub. Co., New York, pp. 162–175.

Gupta, et al., 1978, "Mutation Breeding of chrysanthemum. II. Detection of gamma ray induced mutation in $vM_2$", Nuclear Agric. Biol., 7(2): 50–54.

Das, et al., 1977, "Improvement of some vegetatively propagated ornamentals by gamma radiation", Indian J. Hort. 34(2):169–174.

Searle, et al., 1968, "Chrysanthemums The Year Round", Blanford Press, London, pp. 27–29, 320–327.

Broertjes, 1966, "Mutation breeding of chrysanthemums", Euphytica, 15:156–162.

Dowrick, et al., 1966, "The induction of mutation in chrysanthemum using X-and gamma radiation", Euphytica, 15:204–210.

*Primary Examiner*—Howard J. Locker

*Attorney, Agent, or Firm*—Parkhurst, Wendel & Rossi

[57] ABSTRACT

A new and distinct cultivar of chrysanthemum plant named Coral Reagan, bearing medium sized coral blooms with a yellow-green center and a performance of 24–28 days.

2 Drawing Sheets

This is a continuation of application Ser. No. 07/780,292 filed Oct. 22, 1991, now abandoned.

The present application is related to the following copending applications and patent:

| Application No. | Filing Date | Title |
|---|---|---|
| 07/780,237 | October 22, 1991 | Orange Reagan |
| 08/092,941 | July 19, 1993 | Bronze Reagan |
| 08/088,104 | July 8, 1993 | Dark Reagan |
| 08/092,942 | July 19, 1993 | Sulphur Reagan |
| 08/092,943 | July 19, 1993 | Yellow Reagan |
| 08/088,107 | July 8, 1993 | White Reagan |
| 08/101,278 | August 2, 1993 | Salmon Reagan |
| **Patent No.** | **Issue Date** | **Title** |
| U.S. Plant Pat. No. 8,642 | March 15, 1994 | Reagan |

ORIGIN AND HISTORY OF THE NEW PLANT

The new plant of the present invention comprises a new and distinct cultivar of Chrysanthemum plant which is a naturally occurring sport of a Chrysanthemum named Reagan, which in turn is a cross of unknown *Chrysanthemum morifolium* parents. The Chrysanthemum named Reagan is described in U.S. Plant Pat. No. 8,642. The new cultivar wad discovered in 1988 as a whole plant mutation in Holland, and has been asexually reproduced by cuttings in greenhouses at Ter Aar, Holland. The new cultivar has been found to retin all of its distinctive characterisics through successive propagations.

SUMMARY OF THE NEW PLANT

The present invention is a new and distinct variety of Chrysanthemum of a medium sized bloom and coral color.

BRIEF DESCRIPTION OF THE DRAWINGS

The present new and distinct chrysanthemum cultivar is shown in the accompanying drawings, the color being as nearly true as possible with color photographs of this type.

Sheet 1 shows the full bloom of the new cultivar;

Sheet 2, top, shows various stages of bloom of the new cultivar; and

Sheet 2, bottom, shows the foliage and petiole of the new cultivar.

DESCRIPTION OF THE INVENTION

This new variety of Chrysanthemum is of the botanical classification *Chrysanthemum morifolium,* and is named Coral Reagan. When grown in the vicinity of Ter Aar, Holland, it has a response time of approximately 7½ weeks. This new variety produces medium sized coral blooms with a yellow green center having a 4 week performance (i.e., a vase life of 24–28 days). This new variety of Chrysanthemum has been found to retain its distinctive characteristics throughout successive propagations and may be planted under greenhouse conditions in Holland between weeks fifty and thirty-five (i.e., between December 1 and August 30). Pest resistance, disease resistance and frost tolerance are unknown.

The following is a description of the plant and characteristics (color designations are from R.H.S. Colour Chart) that distinguish it over related known varieties and its antecedents:

Botanical classification:Chrysanthemum morifolium.

Bud:

*Size.*—Medium (cross section±1.0 cm, height ±0.7 cm.

*Form.*—Round and flat.

*Outside color.*—Greyed-purple 186 A.

Bloom:

Size.—Medium.

*Fully expanded.*—6½–7 cm.

Borne.—Upper portion, single flower per peduncle; lower portion, plural flowers per peduncle

*Stems.*—Strong, thick.

*Form.*—Single (daisy).

*Performance.*—Very good 24–30 days; (18°–20° C.).

Color:

*Center of flower.*—Immature: yellow green 151 C; Mature: yellow green 154 A.

*Base of petals.*—Greyed-red 179 C but redder.

*Inside of petals.*—Greyed-red 179 C but redder.

*Reverse of petals.*—Greyed-yellow 162 D tinged with red-purple 71 B Between ribs and margin.

Outer petals.—Greyed-red 179 C but redder.

*Tonality from a distance.*—A pale bronze daisy with a fresh looking center having little or no pollen.

*Discloration.*—Some to yellow orange 23 C.

*Pollen.*—Yellow-orange 14 A.

Petals:

*Texture.*—Upperside smooth, underside smooth.

*Number.*—24–30 (two rows).

*Cross-section.*—Flat, two keels.

*Arrangement.*—Imbricated.

*Persistence.*—Good. Petals keep straight or reflex somewhat at the edge at the end of blooming.

*Fragrance.*—Typical chrysanthemum.

*Disc diameter.*—1.5 cm.

Reproductive organs:

Stamen.—Yellow, thick, 3 nm in length.

*Pollen.*—Appears at a late stage of blooming, yellow-orange in color.

*Styles.*—Green, thick.

*Length.*—±5 mm.

*Stigmas.*—Yellow.

*Width.*—±1 mm.

*Ovaries.*—Enclosed in calyx.

Plant:

*Form.*—Spray mum meant for erect culture. Herbaceous.

*growth.*—Strong.

*Height.*—100–125 cm.

*Peduncle.*—Near the top ±14 cm, near the middle ±24 cm, near the bottom ±28cm.

*Internodes.*—3 cm.

*Flowering response.*7½ weeks.

Foliage:

Color.—Upper side green 137 A, Underside 137 C.

*Size.*—Length ±12 cm, width ±9 cm.

*Quantity.*—22–28.

*Shape.*—Lobed, see photograph.

*Texture.*—Upperside rough, underside smooth slightly hirsute.

*Ribs and veins.*—Ribs well developed, veins not so developed.

*Edge.*—Crenated.

Distinguishing characteristics of the Chrysanthemums of the Reagan family are summarized below in Tables IA and IB. Color designations therein are taken from the R.H.S. Colour Chart.

TABLE IA

| TITLE | REAGAN | WHITE REAGAN |
|---|---|---|
| BUD OUTSIDE COLOR | GREYED-PURPLE 186D BUT PALER | YELLOW 4D |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | PURPLE 75B | WHITE 115D BUT WHITER AND BRIGHTER |
| INSIDE OF PETALS | PURPLE 75B | WHITE 155D BUT WHITER AND BRIGHTER |
| REVERSE OF PETALS | RED-PURPLE 69A BUT PALER | WHITE 155D BUT WHITER AND BRIGHTER |
| OUTER PETALS | PURPLE 75B | WHITE 155D BUT WHITER AND BRIGHTER |
| PETAL CROSS-SECTION | FLAT | FLAT |

| TITLE | CORAL REAGAN | DARK REAGAN |
|---|---|---|
| BUD OUTSIDE COLOR | GREYED-PURPLE 186A | BETWEEN GREYED PURPLE 186A AND B |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | GREYED-RED 179C BUT REDDER | RED-PURPLE 69B LIGHTLY OVER-LAID WITH RED-PURPLE 72A GIVING AN OVERALL IMPRESSION OF PURPLE 75A BUT PINKER |
| INSIDE OF PETALS | GREYED-RED 179C BUT REDDER | RED-PURPLE 69B LIGHTLY OVER-LAID WITH RED-PURPLE 72A GIVING AN OVERALL IMPRESSION OF PURPLE 75A BUT PINKER |
| REVERSE OF PETALS | GREYED-YELLOW 162D TINGED WITH RED-PURPLE 71B BETWEEN RIBS AND MARGIN | RED-PURPLE 69C WITH A LIGHT TESSELLATION OF RED-PURPLE 72A |
| OUTER PETALS | GREYED-RED 179C BUT REDDER | RED-PURPLE 69B LIGHTLY OVER-LAID WITH RED-PURPLE 72A GIVING AN OVERALL IMPRESSION OF PURPLE 75A BUT PINKER |
| PETAL CROSS- | FLAT | CONVEX |

TABLE IA-continued

| SECTION | | |
|---|---|---|
| TITLE | ORANGE REAGAN | BRONZE REAGAN |
| BUD OUTSIDE COLOR | GREYED-RED 180A | GREYED-RED 179C |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | BETWEEN GREYED ORANGE 169A AND B | YELLOW 8A WITH AN OVERLAY OF GREYED RED 179B |
| INSIDE OF PETALS | BETWEEN GREYED ORANGE 169A AND B | YELLOW 8A WITH AN OVERLAY OF GREYED RED 179B |
| REVERSE OF PETALS | NEAREST TO GREYED-ORANGE 163B TINGED WITH RED BETWEEN THE RIBS | YELLOW 8C TINGED ALONG THE CENTER WITH GREYED RED 179B IN A TESSELLATED PATTERN |
| OUTER PETALS | BETWEEN GREYED-ORANGE 169A AND B | YELLOW 8A WITH AN OVERLAY OF GREYED RED 179B |
| PETAL CROSS-SECTION | CONVENX | FLAT |

| TITLE | YELLOW REAGAN | SULPHUR REAGAN |
|---|---|---|
| BUD OUTSIDE COLOR | YELLOW 9C | YELLOW 10C |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | YELLOW 5C | YELLOW 6D |
| INSIDE OF PETALS | YELLOW 5C | YELLOW 6D |
| REVERSE OF PETALS | YELLOW 4C | YELLOW 6D |
| OUTER PETALS | YELLOW 5C | YELLOW 6D |
| PETAL CROSS-SECTION | FLAT | FLAT |

| TITLE | SALMON REAGAN |
|---|---|
| BUD OUTSIDE COLOR | NEAREST TO YELLOW-ORANGE 23D |
| CENTER OF FLOWER | |
| IMMATURE: | YELLOW-GREEN 151C |
| MATURE: | YELLOW-GREEN 154A |
| BASE OF PETALS | NEAREST TO ORANGE 29C |
| INSIDE OF PETALS | NEAREST TO ORANGE 29C |
| REVERSE OF PETALS | NEAREST TO YELLOW-ORANGE 22D |
| OUTER PETALS | NEAREST TO ORANGE 29C |
| PETAL CROSS-SECTION | FLAT |

TABLE IB

| TITLE | REAGAN | WHITE REAGAN |
|---|---|---|
| STEM INFORMATION | | |
| STEM: GREEN COLOR | YELLOW-GREEN 144A | NEAREST GREEN 143C |
| STEM: ANTHOCYANIN COLORATION | ABSENT | ABSENT |
| STEM: STRENGTH | MEDIUM | MEDIUM TO STRONG |
| STEM: BRITTLENESS | PRESENT | PRESENT |
| PEDUNCLE INFORMATION | | |
| LATERAL SHOOT: ATTACHMENT TO STEM | MEDIUM | WEAK TO MEDIUM |
| LATERAL SHOOT: ANGLE BETWEEN LATERAL SHOOT AND STEM | MEDIUM | MEDIUM |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | ROUND | ASYMMETRIC |
| LEAF: APEX | CUSPIDATE | MUCRONATE |
| GROWTH: DIFFERENCE IN AVERAGE LENGTH (IN CMS) | 0 | 0 |
| RESPONSE TIME: DIFFERENCE IN DAYS OF AVERAGE RESPONSE | 0 | 0 |
| RESPONSE ON ALAR: DOSE THAT HAS TO BE USED TO GET AN AVERAGE LENGTH OF ABOUT 90 CMS (DOSE IN GRAMS PER 100 LITER OF WATER) | 300 | 300 |
| YEAR OF DISCOVERY | 1986 | 1989 |

| TITLE | CORAL REAGAN | DARK REAGAN |
|---|---|---|
| STEM INFORMATION | | |
| STEM: GREEN COLOR | YELLOW-GREEN 144A | YELLOW-GREEN 144A |
| STEM: ANTHOCYANIN COLORATION | PRESENT | PRESENT |
| STEM: STRENGTH | MEDIUM | MEDIUM |
| STEM: BRITTLENESS | ABSENT | PRESENT |
| PEDUNCLE INFORMATION | | |
| LATERAL SHOOT: ATTACHMENT TO STEM | WEAK TO MEDIUM | MEDIUM |
| LATERAL SHOOT: ANGLE BETWEEN LATERAL SHOOT AND STEM | SMALL | MEDIUM |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | ASYMMETRIC | ASYMMETRIC |
| LEAF: APEX | CUSPIDATE | MUCRONATE |

TABLE IB-continued

| | | |
|---|---|---|
| GROWTH: DIFFERENCE IN AVERAGE LENGTH (IN CMS) | −5 | 0 |
| RESPONSE TIME: DIFFERENCE IN DAYS OF AVERAGE RESPONSE | +1 | +½ |
| RESPONSE ON ALAR: DOSE THAT HAS TO BE USED TO GET AN AVERAGE LENGTH OF ABOUT 90 CMS (DOSE IN GRAMS PER 100 LITER OF WATER) | 250 | 300 |
| YEAR OF DISCOVERY | 1988 | 1988 |
| TITLE | ORANGE REAGAN | BRONZE REAGAN |
| STEM INFORMATION | | |
| STEM: GREEN COLOR | BETWEEN YELLOW-GREEN 144A AND 146B | YELLOW-GREEN 144A |
| STEM: ANTHOCYANIN COLORATION | PRESENT | PRESENT |
| STEM: STRENGTH | MEDIUM | MEDIUM |
| STEM: BRITTLENESS | PRESENT | ABSENT |
| PEDUNCLE INFORMATION | | |
| LATERAL SHOOT: ATTACHMENT TO STEM | MEDIUM | WEAK |
| LATERAL SHOOT: ANGLE BETWEEN LATERAL SHOOT AND STEM | SMALL | SMALL |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | TRUNCATE | ASYMMETRIC |
| LEAF: APEX | CUSPIDATE | CUSPIDATE |
| GROWTH: DIFFERENCE IN AVERAGE LENGTH (IN CMS) | +10 | 0 |
| RESPONSE TIME: DIFFERENCE IN DAYS OF AVERAGE RESPONSE | −1 | −½ |
| RESPONSE ON ALAR: DOSE THAT HAS TO BE USED TO GET AN AVERAGE LENGTH OF ABOUT 90 CMS (DOSE IN GRAMS PER 100 LITER OF WATER) | 450 | 250 |
| YEAR OF DISCOVERY | 1988 | 1988 |
| TITLE | YELLOW REAGAN | SULPHUR REAGAN |
| STEM INFORMATION | | |
| STEM: GREEN COLOR | YELLOW-GREEN 146B | NEAREST GREEN 143C |
| STEM: ANTHOCYANIN COLORATION | ABSENT | ABSENT |
| STEM: STRENGTH | MEDIUM | MEDIUM TO STRONG |
| STEM: BRITTLENESS | ABSENT | ABSENT |

TABLE IB-continued

| | | |
|---|---|---|
| PEDUNCLE INFORMATION | | |
| LATERAL SHOOT: ATTACHMENT TO STEM | WEAK TO MEDIUM | WEAK TO MEDIUM |
| LATERAL SHOOT: ANGLE BETWEEN LATERAL SHOOT AND STEM | SMALL | SMALL |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | PARALLEL | PARALLEL |
| LEAF: SHAPE OF BASE | ASYMMETRIC | ASYMMETRIC |
| LEAF: APEX | MUCRONATE | MUCRONATE |
| GROWTH: DIFFERENCE IN AVERAGE LENGTH (IN CMS) | 0 | +10 |
| RESPONSE TIME: DIFFERENCE IN DAYS OF AVERAGE RESPONSE | +1 | −1 |
| RESPONSE ON ALAR: DOSE THAT HAS TO BE USED TO GET AN AVERAGE LENGTH OF ABOUT 90 CMS (DOSE IN GRAMS PER 100 LITER OF WATER) | 280 | 450 |
| YEAR OF DISCOVERY | 1990 | 1990 |
| TITLE | SALMON REAGAN | |
| STEM INFORMATION | | |
| STEM: GREEN COLOR | YELLOW GREEN 144A | |
| STEM: ANTHOCYANIN COLORATION | PRESENT | |
| STEM: STRENGTH | MEDIUM | |
| STEM: BRITTLENESS | PRESENT | |
| PEDUNCLE INFORMATION | | |
| LATERAL SHOOT: ATTACHMENT TO STEM | MEDIUM | |
| LATERAL SHOOT: ANGLE BETWEEN LATERAL SHOOT AND STEM | MEDIUM | |
| ADDITIONAL FOLIAGE INFORMATION | | |
| LEAF: SHAPE OF BASE OF SINUS BETWEEN LATERAL LOBES | ROUND | |
| LEAF: MARGINS OF SINUS BETWEEN LATERAL LOBES | PARALLEL | |
| LEAF: SHAPE OF BASE | ASYMMETRIC | |
| LEAF: APEX | CUSPIDATE | |
| GROWTH: DIFFERENCE IN AVERAGE LENGTH (IN CMS) | +10 | |
| RESPONSE TIME: DIFFERENCE IN DAYS OF AVERAGE RESPONSE | 0 | |
| RESPONSE ON ALAR: DOSE THAT HAS TO BE USED TO GET AN AVERAGE LENGTH OF ABOUT 90 CMS (DOSE IN GRAMS PER 100 LITER OF WATER) | 350 | |
| YEAR OF DISCOVERY | 1987 | |

What is claimed:

1. A new and distinct cultivar of Chrysanthemum plant named Coral Reagan, as described and illustrated.

* * * * *

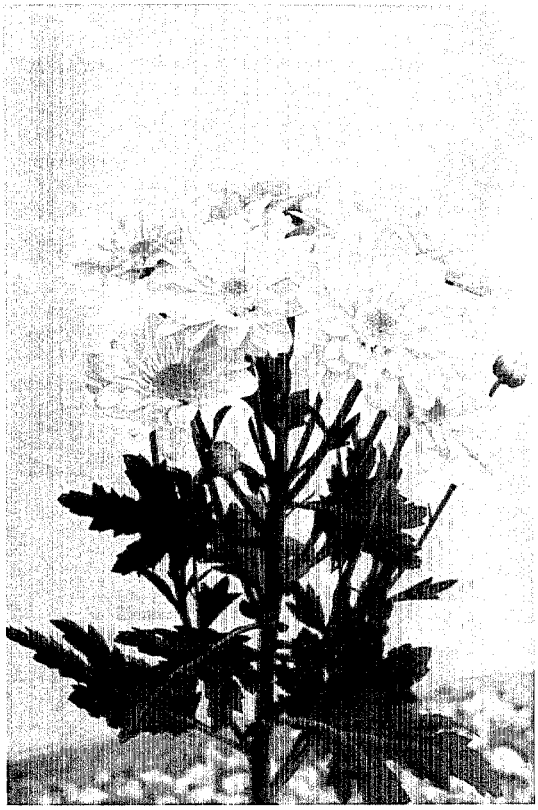

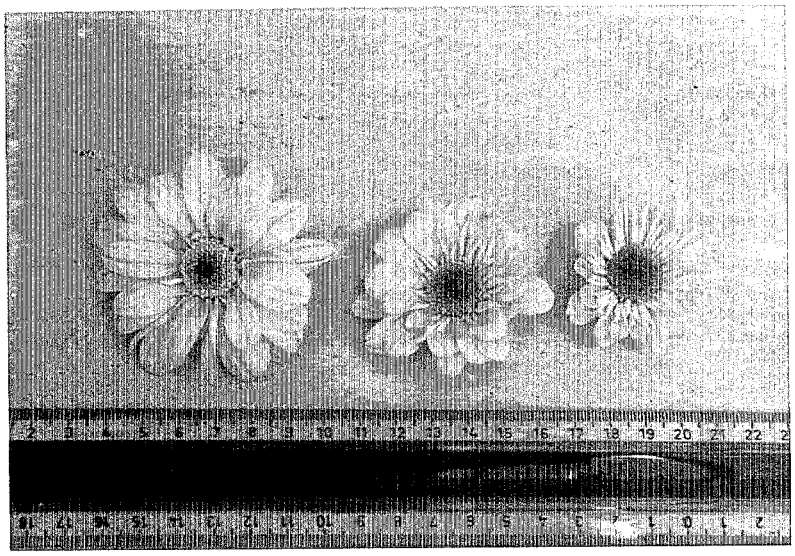
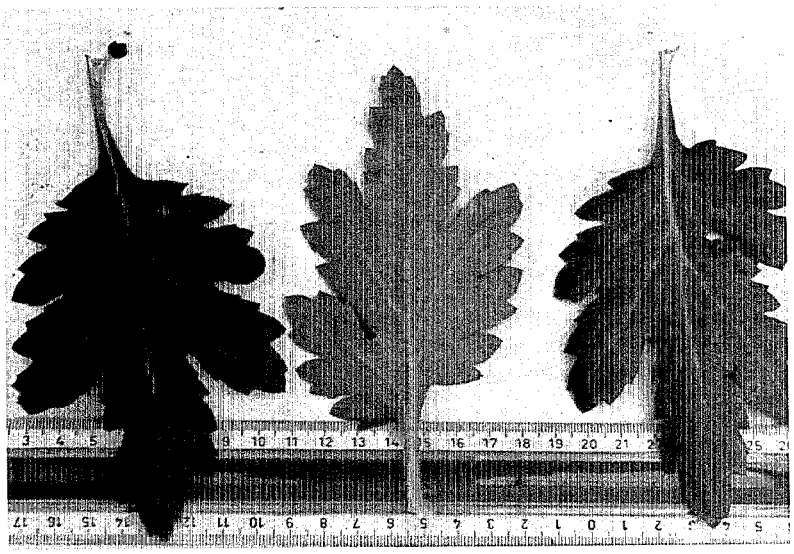

UNITED STATES PATENT AND TRADEMARK OFFICE

CERTIFICATE OF CORRECTION

PATENT NO. : Plant 8,974

DATED : November 8, 1994

INVENTOR(S) : Martinus Van der Jagt

It is certified that error appears in the above-indentified patent and that said Letters Patent is hereby corrected as shown below:

On the title page: Item [22], change "August 29, 1993" to --August 2, 1993--.

Signed and Sealed this

Twenty-first Day of February, 1995

*Attest:*

Bruce Lehman

BRUCE LEHMAN

*Attesting Officer*

*Commissioner of Patents and Trademarks*